United States Patent
Chu et al.

(10) Patent No.: US 9,626,754 B2
(45) Date of Patent: Apr. 18, 2017

(54) SYSTEM, APPARATUS AND METHOD FOR DISPENSED ADHESIVE MATERIAL INSPECTION

(71) Applicants: Quyen Duc Chu, St. Petersburg, FL (US); Nazir Ahmad, St. Petersburg, FL (US)

(72) Inventors: Quyen Duc Chu, St. Petersburg, FL (US); Nazir Ahmad, St. Petersburg, FL (US)

(73) Assignee: JABIL CIRCUIT, INC., St. Petersburg, FL (US)

( * ) Notice: Subject to any disclaimer, the term of this patent is extended or adjusted under 35 U.S.C. 154(b) by 0 days.

(21) Appl. No.: 14/724,617

(22) Filed: May 28, 2015

(65) Prior Publication Data

US 2016/0350909 A1 Dec. 1, 2016

(51) Int. Cl.
*G03F 7/00* (2006.01)
*G06T 7/00* (2017.01)
*H04N 5/225* (2006.01)

(52) U.S. Cl.
CPC .......... *G06T 7/0008* (2013.01); *G06T 7/0081* (2013.01); *G06T 7/0085* (2013.01);
(Continued)

(58) Field of Classification Search
CPC ............... G06T 7/0004; G06T 7/001; G06T 2207/30148; G06T 2207/30164; G06T 7/0006; G06T 7/0008; G06T 7/0081; G06T 7/0085; G06T 2207/10141; G06T 2207/30108; H04N 5/2256
(Continued)

(56) References Cited

U.S. PATENT DOCUMENTS 5,949,905 A * 9/1999 Nichani ................... G06K 9/38
382/171
6,069,693 A * 5/2000 Licchesi ................ G01N 21/88
356/237.1

(Continued)

FOREIGN PATENT DOCUMENTS

EP          1025968 B1    11/2004
KR   10-2014000004 4       1/2014

OTHER PUBLICATIONS

International Search Report and Written Opinion dated Oct. 12, 2016 for PCT/2016/034557.

*Primary Examiner* — Sheela C Chawan
(74) *Attorney, Agent, or Firm* — Barnes & Thornburg LLP; Thomas J. McWilliams

(57) ABSTRACT

Apparatus, system and method for detecting defects in an adhesion area that includes an adhesive mixed with a fluorescent material. One or more illumination devices may illuminate the fluorescent material in the adhesion area with a light of a predetermined wavelength. A camera may be configured to capture an image of the illuminated adhesion area. A processing device, communicatively coupled to the camera, may be configured to process the captured image by applying one or more boundary areas to the captured image and determining an image characteristic within each of the boundary areas, wherein the image characteristic is used by the processing device to determine the presence of a defect in the adhesive, such as an excess of adhesive or an insufficient application of adhesive.

29 Claims, 5 Drawing Sheets

(52) U.S. Cl.
CPC . *H04N 5/2256* (2013.01); *G06T 2207/10064* (2013.01); *G06T 2207/10141* (2013.01); *G06T 2207/30108* (2013.01)

(58) Field of Classification Search
USPC ..... 382/141; 430/257, 253, 260, 49.31, 138, 430/256, 254, 117.5, 527, 325
See application file for complete search history.

(56) References Cited

U.S. PATENT DOCUMENTS

| | | | |
|---|---|---|---|
| 6,778,046 B2* | 8/2004 | Stafford | B81B 7/0077 200/181 |
| 7,503,988 B2* | 3/2009 | Hayashi | G02F 1/1333 156/106 |
| 9,283,799 B2* | 3/2016 | Koga | G06K 19/07 |
| 2013/0064967 A1 | 3/2013 | Feinstein et al. | |

* cited by examiner

SYSTEM, APPARATUS AND METHOD FOR DISPENSED ADHESIVE MATERIAL INSPECTION

FIELD OF THE DISCLOSURE

The present disclosure relates to material additives and inspection. More specifically, the present disclosure relates to adhesive processing and automated optical inspection (AOI) for manufactured products/devices.

BACKGROUND

In manufacturing apparatuses and systems, the ability to inspect dispensed adhesives, especially during a final assembly of a product, becomes important as the product yield loss at this stage may be exceedingly costly. In addition to ensuring that proper adhesion has been applied, adhesively bonded interfaces for materials on a product visibly impact the cosmetics and perceived quality of a product. If excessive adhesive compounds are visible around edges or periphery of a device (e.g., integrated circuit, mechanical device, display, etc.) affixed to a product, this may not only affect the integrity of the adhesion, but further provide the impression to a user that the product is of inferior quality.

Of course, manual visual inspections have long been utilized to inspect quality of products. However, such inspections are often slow to conduct and are prone to human error. Furthermore, in certain cases, adhesives may be transparent or colored to match the bonding surface, which makes human optical inspection more difficult. Accordingly, an effective quality control and inspection technology is needed to provide improved inspection of devices that have been affixed to a surface using an adhesive.

SUMMARY

Accordingly, under some exemplary embodiments, a system is disclosed for detecting defects in an adhesion area comprising an adhesive mixed with a fluorescent material, comprising one or more illumination devices for illuminating the fluorescent material in the adhesion area with a light of a predetermined wavelength. A camera may be configured to capture an image of the illuminated adhesion area. A processing device, communicatively coupled to the camera, may be configured to process the captured image by applying one or more boundary areas to the captured image and determining an image characteristic within each of the boundary areas, wherein the image characteristic is used by the processing device to determine the presence of a defect in the adhesive.

In other illustrative embodiments, a method is disclosed for detecting defects in an adhesion area comprising an adhesive mixed with a fluorescent material, comprising illuminating, by one or more illumination devices, the fluorescent material in the adhesion area with a light of a predetermined wavelength, capturing an image of the illuminated adhesion area by a camera, processing, by a processing device communicatively coupled to the camera, the captured image by applying one or more boundary areas to the captured image, determining, by the processing device, an image characteristic within each of the boundary areas, and using the image characteristic to determine the presence of a defect in the adhesive by the processing device.

BRIEF DESCRIPTION OF THE FIGURES

The present disclosure will become more fully understood from the detailed description given herein below and the accompanying drawings which are given by way of illustration only, and which thus do not limit the present disclosure, and wherein.

DETAILED DESCRIPTION

Figure 1:
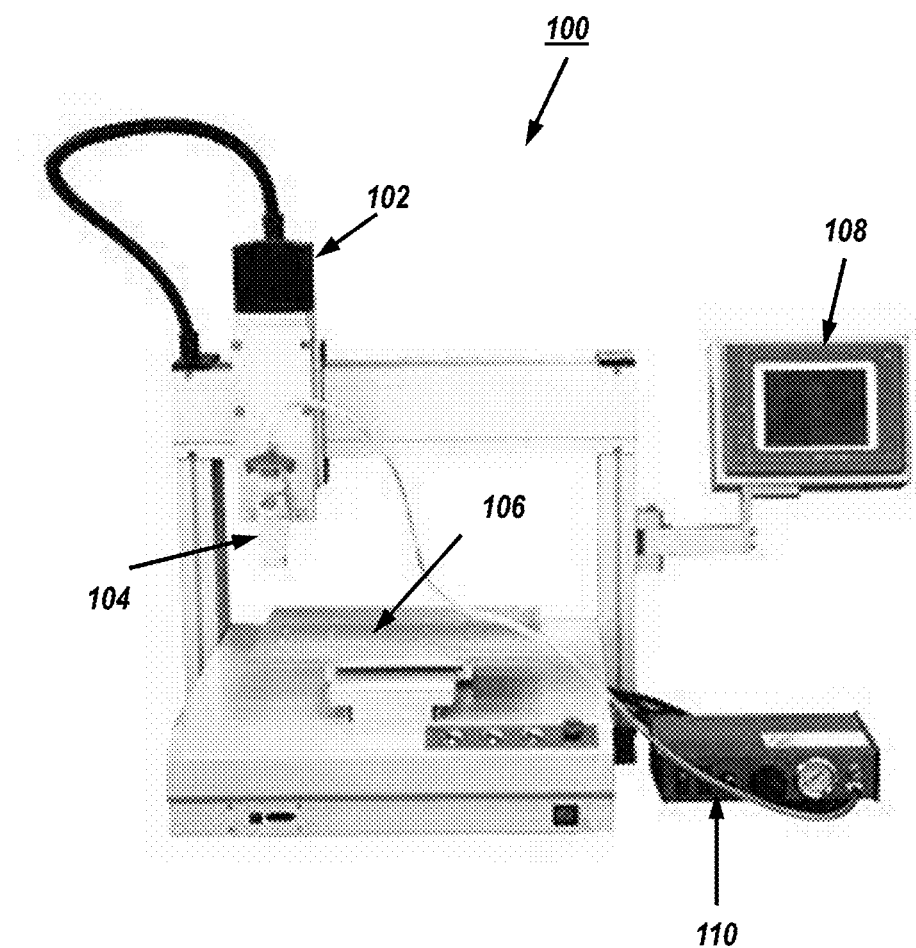
FIG. 1 shows an illustrative adhesive dispenser for dispensing adhesive on a surface positioned on an adhesive dispenser table under an embodiment.

The figures and descriptions provided herein may have been simplified to illustrate aspects that are relevant for a clear understanding of the herein described devices, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

Turning now to FIG. 1, an illustrative embodiment is shown of an adhesive dispenser 100, which, in this example, is a table adhesive dispenser. It should be understood by those skilled in the art that the particular configuration of dispenser 100 is shown for the purposes of illustrative purposes only, and is not intended to be limiting in any way. Any suitable dispenser, such as a single or plural station dispenser, and/or single- or plural-axis (e.g., 3-axis, 6-axis) dispenser may readily be used without departing from the scope of the present disclosure.

Dispenser 100 of FIG. 1 comprises a display 108, which may comprise a computer that may be used to program dispenser 100. Dispensing pump 110 may be any suitable pump (e.g., time/pressure pump, auger pump, piston pump, etc.) for viscous fluids and may be coupled to nozzle 104 that may dispense adhesive material onto a device positioned on working surface 106 with the assistance of dispensing mechanism 102. Dispensing pump 110 may be coupled to an adhesive storage tank (not shown) that stores adhesive compounds for pump 110. Dispenser 100 may be configured to provide adhesives or other material for a wide variety of applications including, but not limited to, mechanical parts coating, cell phone buttons point glue, mobile phone battery packaging, laptop battery package, coil point glue, PCB bond fixed sealant, IC sealant, horn external punctuate glue, PDA sealant, LCD sealant, IC packaging, IC bonding, casing bonding, optical device processing, mechanical seal, and so forth. The applications may further include tongue-in-groove adhesion, lap shear, and joints under tensile, peel, or cleavage stress. In cases where cosmetic considerations are important, matched colors may be used for adhesion. For example, a black adhesive (e.g., epoxy or polyurethane) may be used on a black anodized aluminum surface, and/or a clear adhesive may be used on a transparent polycarbonate or liquid crystal polymer.

A device positioned on working surface 106 may be positioned using computer-assisted positioning technologies known in the art to ensure that adhesives and/or other material is being applied in a proper area. The device surface for receiving viscous material from nozzle 104 may be any suitable material, including polycarbonate (PC) material, glass-filled PC, liquid crystal polymer (LCP), glass-reinforced epoxy laminate (FR-4) sheets, tubes, rods and printed circuit boards (PCB), solder mask surfaces, aluminum, titanium, gold, copper, silicon, steel, stainless steel, etc. The viscous fluid (e.g., adhesive) dispensed from nozzle 104 may comprise epoxy adhesives, polyurethanes (PUR) and/or acrylics, silicones, hot melts, thermally or radiation-cured, etc. Additionally applicable fluid may comprise silica gel, EMI conductive adhesive, UV glue, AB glue, fast dry glue, sealant, grease, silver glue, red glue, solder paste, cooling paste, prevent solder paste, transparent lacquer, screw fixation agent, etc.

In an exemplary embodiment, the viscous material, such as adhesive, is mixed with a fluorescing additive, which would cause the material to fluoresce when illuminated with a light of a predetermined wavelength (e.g., UV light, IR light, etc.). In certain embodiments, the fluorescing additive may comprise less than 1% by weight of the adhesive-dye mixture in order to maintain the integrity of the adhesive. However, depending on the type of adhesive used and adhesive properties, greater amounts of fluorescing additive may be used as well. The specific fluorescing additive may vary depending on the application, and may be made from, contain, or be based one or more of a variety of dyes including, but not limited to, Acridine dyes, Cyanine dyes, Fluorone dyes, Oxazine dyes, Phenanthridine dyes, and Rhodamine dyes.

Figure 2A:
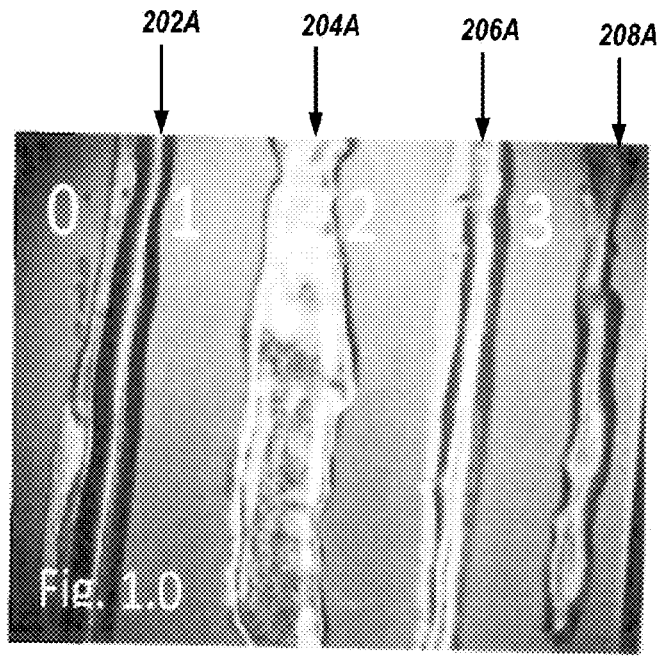
FIG. 2A shows a plurality of adhesives dispensed onto a surface.
Figure 2B:
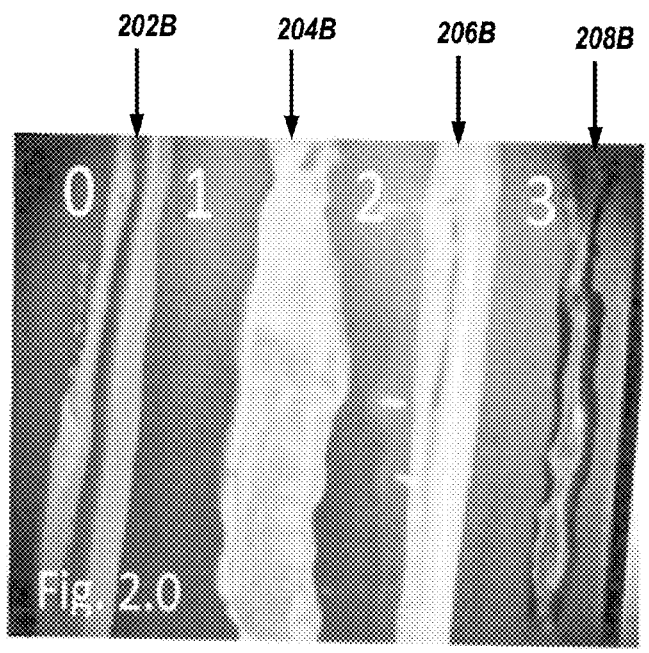
FIG. 2B shows the plurality of adhesives of FIG. 2A excited by a light comprising a predetermined optical wave band after the adhesives are mixed with a fluorescent material under an illustrative embodiment.

FIGS. 2A and 2B provide illustrative examples some effects of adding fluorescent additives to adhesives. In the example of FIG. 2A, an epoxy is shown with four different fluorescent dye additives (202A, 204A, 206A, 208A), which have not been exposed to any specialized illumination. FIG. 2B shows the example of FIG. 2A exposed to UV light, where the additives (202B, 204B, 206B, 208B) fluoresces and can be seen visibly. Of course, such a configuration advantageously assists in manual visual inspection, and will allow an inspector to visually see apparent defects in an adhesion process. However, the fluorescent additive may be advantageously used for Automated Optical Inspection (AOI) systems for use in defect detection.

Figure 3:
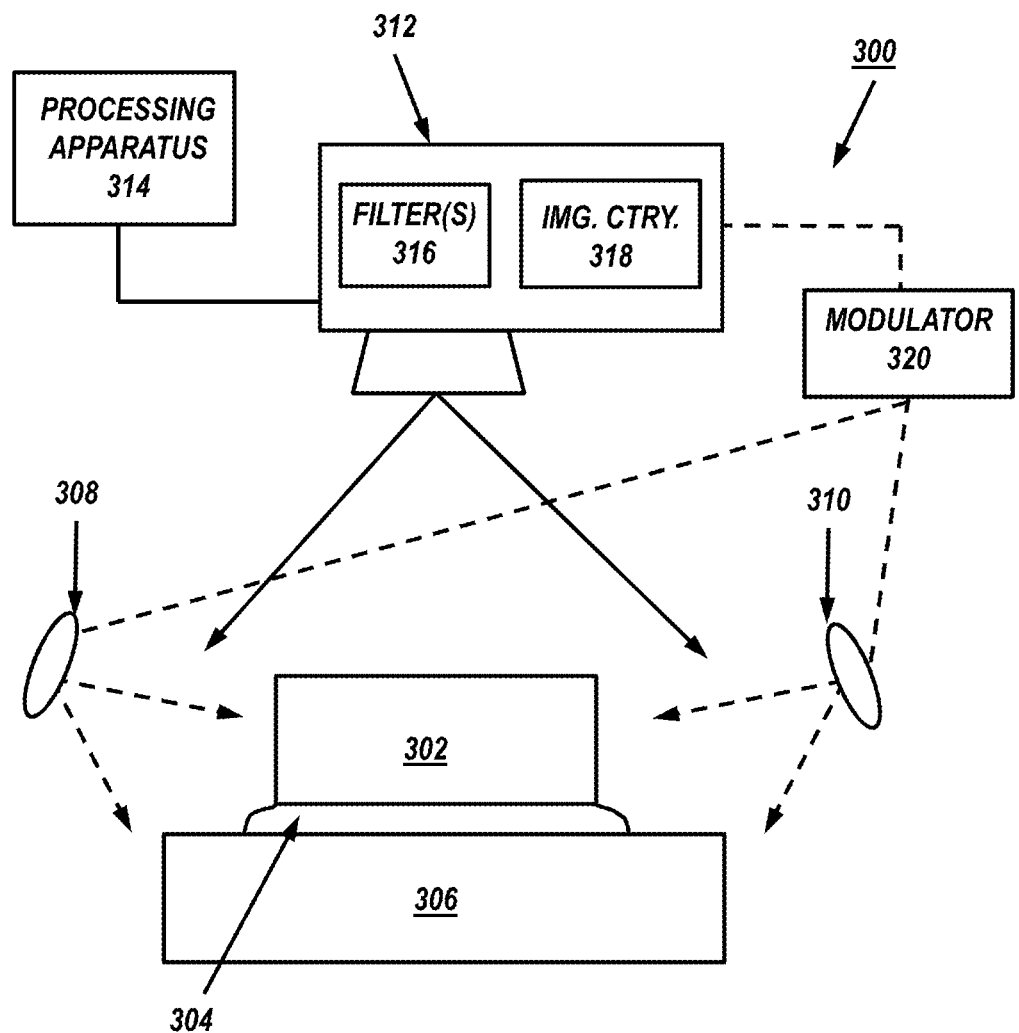
FIG. 3 shows a camera coupled to a processing apparatus for optically inspecting a dispensed adhesive between a device and a surface, wherein an area around the dispensed adhesive is illuminated to excite the fluorescent material under an illustrative embodiment.

The illustrative embodiment of FIG. 3 shows a simplified AOI system 300, wherein an object 302 is adhered to a work surface 306 using adhesive 304. The object may be any suitable object configured for adhesion including, but not limited to, a material, object, and/or circuit. In an exemplary embodiment, adhesive 304 is an adhesive such as those described above comprising a fluorescing additive. The system 300 may further comprise a camera 312 coupled to a processing apparatus 314, such as a computer or workstation, where the camera 312 may be positioned to image the object 302, adhesive 304 and work surface 306 (collectively referred to herein as an "adhesion area") while one or more illuminating lights 308, 310 illuminate the adhesion area with a light comprising one or more predetermined wavelengths (e.g., UV, IR).

While the illustrative embodiment of FIG. 3 shows two illuminating lights 308, 310, it should be understood that multiple lighting configurations are contemplated in the present disclosure. For example, a single light may be used in one embodiment. In another embodiment, three or more lights may be used depending on the fluorescent properties of the adhesive 304 and contrast between the object 302 and work surface 306. In another illustrative embodiment, one or more lights may be incorporated into the camera 312 and used for illumination. Additionally, a modulator 320 may be utilized in embodiments where one or more of the illuminating lights 308, 310 are modulated to affect the frequency or phase of illuminating light, described in greater detail below. The modulator 320 may be coupled directly to camera 312, which in turn creates an indirect connection to processing apparatus 314. Alternately, the modulator 320 may bypass the camera 312 and be directly connected to processing apparatus 314.

Camera 312 may be embodied as a silicon-based camera, such as a charge-coupled (CCD) camera or active pixel sensors in complementary metal-oxide semiconductor (CMOS) or N-type metal-oxide semiconductor (NMOS, Live MOS) technologies. In some illustrative embodiments, camera 312 may be configured as a dual-camera arrangement to accommodate stereo vision, which may increase accuracy. Camera 312 may further comprise one or more filters 316 and imaging circuitry 318, which may further include processors and other circuitry for processing images locally on camera 312. In some illustrative embodiments, filters 316 may be embodied as fixed and/or removable optical filters that may pass and/or block predetermined wavelengths of light when camera 312 takes images of the adhesion area.

In some illustrative embodiments, camera 312 may be coupled to processing apparatus 314, such as a computer, which may be configured to provide control signals to control operation of camera 312, and process images received from camera 312. Processing apparatus 314 may be a stand-alone device, or may further comprise communication circuitry to communicate over a network (e.g., WAN, LAN) in a wired or wireless manner. Processing apparatus 314 may further be equipped with software allowing it to apply filters, masks and/or boundaries to the images taken by camera 312, and may further allow processing apparatus 314 to detect characteristics of images received from camera 312 to detect potential defects in an adhesion area.

Prior to imaging, it is preferable to calibrate the system 300 to ensure that the most accurate fluorescent signal is being received by camera 312. The strength of a fluorescence signal (i.e. the fluorescence signal to noise ratio) is dependent upon a number of different parameters. For one, the amount of fluorescent dye present in the adhesive will determine the strength of the signal. Another way to increase the fluorescence signal to noise ratio is to increase the amount of light used to excite fluorescence. A third way to increase the fluorescence signal to noise ratio is to increase the sensitivity of the camera 312.

In an illustrative embodiment, camera 312 may be configured as a camera utilizing time-of-flight (TOF) imaging with or without the assistance of processing device 312. TOF imaging technology works by measuring the phase shift between emitted and detected infrared light at a high modulation frequency. In an illustrative embodiment, the camera 312 may utilize lighting, such as LEDs or other suitable lighting, that emits light modulated at a higher frequency (e.g., 1-20 MHz), where this light then reflects off objects (e.g., fluoresced adhesive) in the adhesion area and is detected by the camera. In an illustrative embodiment, the camera may use a combination of an infrared band-pass optical filter and a multi-bin (e.g., four-bin) lock-in detection scheme for each of the pixels to ensure that it is able to pick out what part of the total signal it receives is modulated at the given frequency (e.g., 1-20 MHz) and in the infrared. The phase shift between the emitted and detected signals is then used, in conjunction with the speed of light, to calculate the distance at which the reflection occurred for all pixels resulting in a distance image. Those skilled in the art will appreciate that these techniques may be replicated in other light wavebands as well.

Utilizing TOF, camera 312 may be configured to acquire fluorescence images by configuring the electric signal, to be sent to an LED of the proper power and fluorescence excitation wavelength light (e.g., 308, 310). A short pass filter (e.g., <800 nm), or other suitable filter, may be used in front of the LED (e.g., 308, 310) to ensure that photons emitted by the LED would not be mistaken for fluorescence. In some illustrative embodiments, the camera 312 may be configured with a long-pass filer (e.g., >800 nm), or other suitable filter, to ensure that the camera only sees the fluorescence signal. This configuration will allow for the fluorescence signal to be detected while suppressing the non-fluorescent background. An advantage of this camera configuration for fluorescence imaging is that the high modulation and detection frequency allows for all lower frequency noise, normally present in a fluorescence image, to be reduced or eliminated from the image. Pushing the desired fluorescent signal to a higher frequency (e.g., 1-20 MHz) consequently minimizes the region for noise, thus increasing the sensitivity of camera 312 to the fluorescence signal.

Because only a small number of the excitation photons stimulate fluorescence, and fluorescent photons may be emitted in all directions, the optical power of the fluorescence signal can be three or four orders of magnitude smaller than the excitation signal. Thus being able to distinguish fluorescent photons from other, and often much brighter, sources of light may be important for acquiring a good fluorescence image.

Under an illustrative embodiment, the fluorescence signal may be distinguished from other sources of light by utilizing lock-in detection which may be accomplished by modulating the fluorescence signal at one frequency and detecting only the signal that occurs at this frequency or frequency range. The amount of noise that can be eliminated with this technique may be dependent on the frequency of modulation. The less common the noise is at the frequency of modulation, the better the signal to noise ratio.

Figure 4:
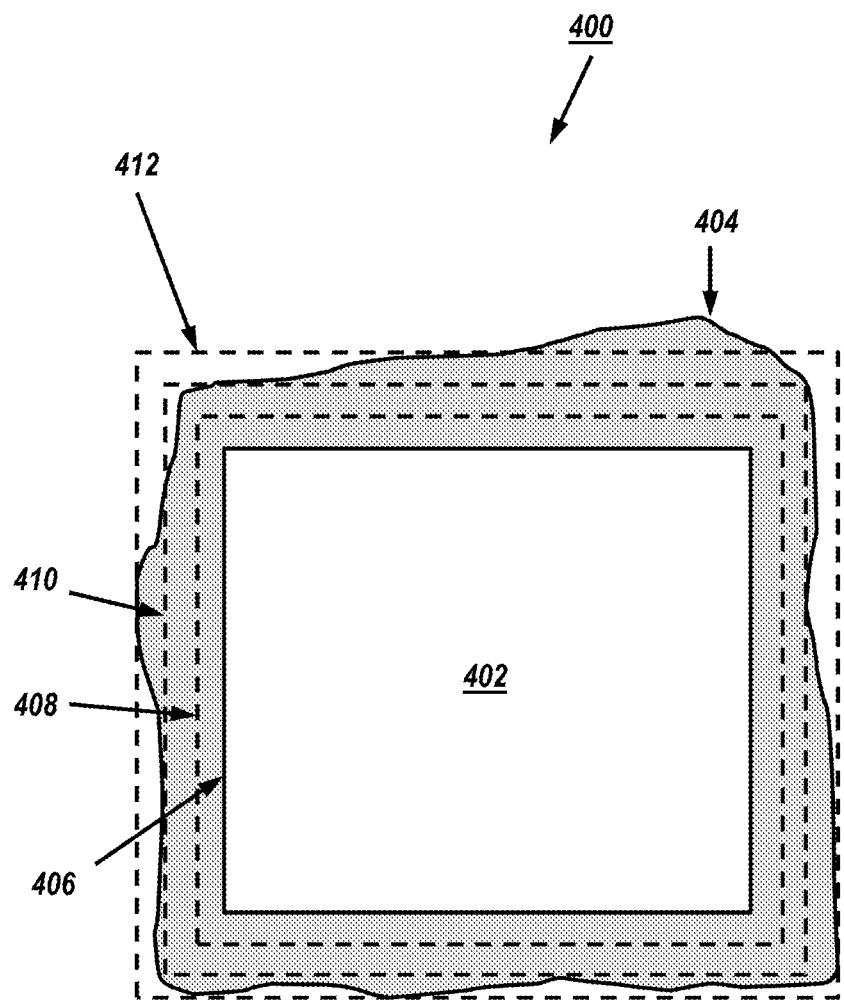
FIG. 4 illustrates a plurality of boundary/mask areas used by a processing apparatus for optical inspection using the embodiment of FIG. 3 to determine one or more characteristics of dispensed adhesive under an illustrative embodiment.

In some illustrative embodiments, processing apparatus 312 may utilize mask or boundary processing to process regions of interest of an adhesion area imaged by camera 312. Turning to FIG. 4, an illustrative embodiment is shown of a simulated image 400 captured by camera 312 of an object 402 affixed to a surface using adhesive 404 which has been mixed with a fluorescent dye and illuminated as described above. Processing apparatus 314 may partition the image 400 into one or more boundaries or regions 406-410, where the area in each boundary (e.g., 406-408, 408-410, 410-412) may be processed to determine one or more image characteristics, demonstrating the presence (or absence) of illuminated adhesive, which in turn may indicate a defect in the application of adhesive.

Figure 5:
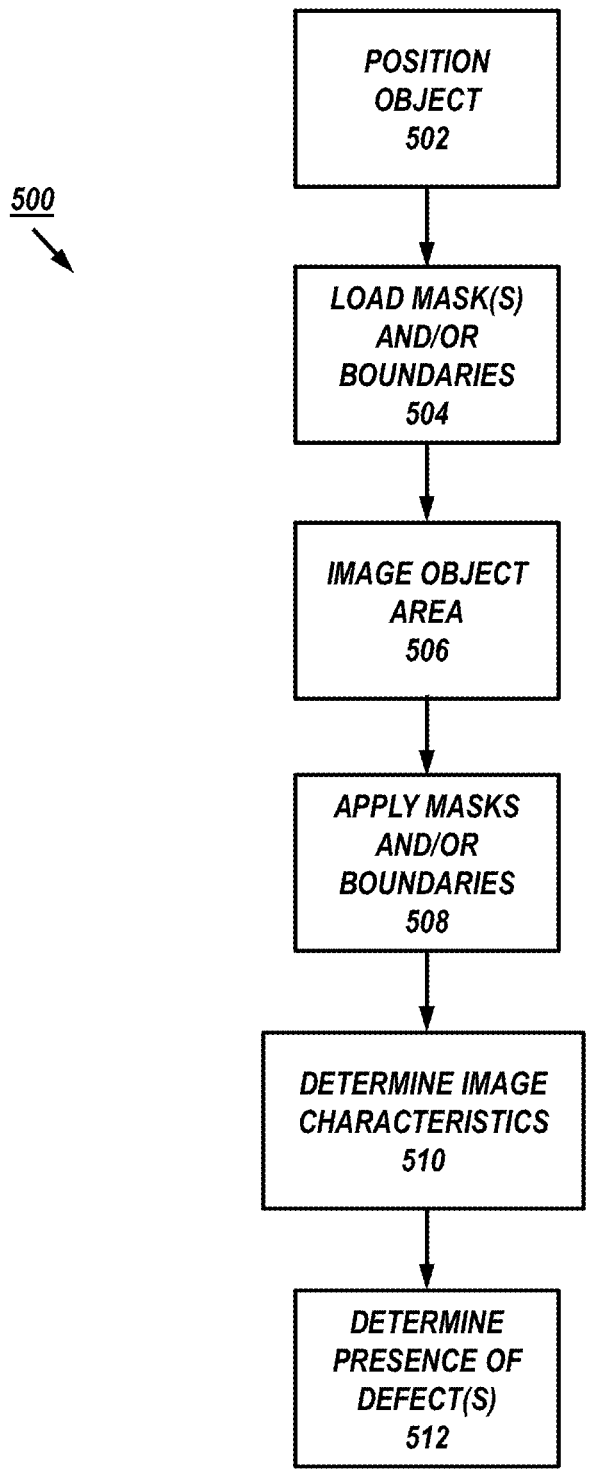
FIG. 5 shows an illustrative method for capturing and processing images and to determine image characteristics for determining potential defects under an embodiment.

Turning to FIG. 5, an illustrative AOI method 500 is shown for processing fluoresced images under one embodiment. In block 502, an AOI system (e.g., system 300) positions an object for imaging. The positioning may be accomplished using manual techniques, automated techniques, or a combination of both as is known in the art. The positioning in block 502 is done so that camera 312 may accurately capture image areas of interest, such as an adhesion area. In block 504, the system (e.g., 300) loads or executes one or more masks and/or boundaries for the image to taken by camera 312 in block 506.

As illustrated in FIG. 4, the masks/boundaries of method 500 may be applied to set boundaries or areas for image processing, and/or to restrict (mask) other areas for an iterative image processing procedure. In one simplified example, processing apparatus 312 may perform image processing by analyzing a first peripheral boundary, defined by the edge of object 402 to first boundary 406 to determine the coverage of adhesion (e.g., image pixel coverage) in this area. The processing apparatus 312 may then move to the next boundary region defined by the outer periphery of boundary 408 and inner periphery of boundary 410 to determine the coverage of adhesion (e.g., image pixel coverage) in this area, and then to the next boundary region defined by the outer periphery of boundary 410 and inner periphery of boundary 412 to determine the coverage of adhesion in a similar manner.

It should be understood by those skilled in the art that multiple variations of the example provided above are contemplated by the present disclosure. For example, a greater or lesser amount of boundaries may be used by processing apparatus 314. In another example, certain boundary regions may be masked (e.g., 406-408, 408-410) while one or more regions are being processed (e.g., 410-412). This configuration may be advantageous in that the processing apparatus 314 may focus on specific areas of the adhesion area that may be susceptible to defects.

Referring still to FIG. 5, once the masks and/or boundaries are loaded in block 504, the camera (e.g., camera 312) takes an image of the object(s) in the adhesion area in block 506, and the masks and/or boundaries may be applied in block 508, as described above. Depending on the resolution of the camera and size of the adhesion area, boundaries may be set in increments of one or more centimeters, millimeters or micrometers. It should be understood by those skilled in the art that the order of loading and applying masks relative to the imaging in block 506 may be modified. For example, the loading and application of masks and/or boundaries may occur after the image is taken in an illustrative embodiment.

In block 510, the processing apparatus 314 processes the image to determine image characteristics using machine vision algorithms, and determines, using the image characteristics, if potential defects are present in block 512. In one illustrative embodiment, processing apparatus 314 may simply calculate the coverage of illuminated pixels relative to an area in a boundary region, which would correspond to adhesive coverage in the area. Utilizing any of maximum and/or minimum thresholds, the processing apparatus 314 may determine if potential defects exist. For example, in a given adhesive application, it may be known that certain values should be present in a given boundary region. Thus, referring to the illustrative embodiment of FIG. 4, processing apparatus 314 may determine from an image that an inner boundary area (e.g., between 406 and 408) has only 92% pixel coverage for the image boundary area, which would indicate only a 92% adhesive coverage. Since the adhesion application in this example is expected to have full coverage (i.e., 100%), since it is so close to the periphery of the object 402, having a lesser amount may indicate to processing apparatus that insufficient or defective adhesive is present.

Similarly, an intermediate or outer boundary region (e.g., between 408 and 410, or 410 and 412) may be processed to determine if adequate adhesive coverage is present. For example, as the boundary region between 410 and 412 is on the outer edges of the periphery, the adhesive coverage (or "spread") in the area may be non-uniform but expected to be a lesser amount (e.g., covering 50%) for the entire boundary area. Setting an appropriate threshold value or range (e.g., 40-60%), the pixel coverage detection may be calculated by processing device 312 such that amounts greater and/or less than the threshold(s) indicates an excessive or insufficient adhesive coverage defect. In another example, the processing device 312 may be configured to detect defects on an absolute boundary threshold. For example, any detection of adhesive outside a boundary threshold automatically signals a defective adhesive application.

Since the fluorescing adhesive advantageously provides a greater optical contrast, other, more sophisticated machine vision techniques may be utilized. For example, processing device 312 may utilize edge detection techniques to analyze specific adhesive shapes, with or without the use of boundaries and masks. Edge detection may comprise search-based or zero-crossing based techniques. A search-based approach detects edges by first computing a measure of edge strength, usually a first-order derivative expression such as the gradient magnitude, and then searches for local directional maxima of the gradient magnitude using a computed estimate of the local orientation of the edge, usually the gradient direction. The zero-crossing based approach searches for zero crossings in a second-order derivative expression computed from the image in order to find edges, usually the zero-crossings of the Laplacian or the zero-crossings of a non-linear differential expression. As a pre-processing step to edge detection, a smoothing stage, such as Gaussian smoothing, may be applied. Other illustrative machine vision techniques include, but are not limited to, grayscale matching, gradient matching, and the like.

It can be appreciated by those skilled in the art that the use of fluorescing additives to adhesives provides an advantageous configuration for inspecting for defects, particularly in automated optical inspection systems utilizing machine learning algorithms. Utilizing TOF cameras also provides additional, accurate, image property detection while minimizing costs, as TOF cameras are readily available, inexpensive, and may be easily modified for automated optical inspection purposes.

In the foregoing detailed description, it can be seen that various features are grouped together in individual embodiments for the purpose of brevity in the disclosure. This method of disclosure is not to be interpreted as reflecting an intention that the subsequently claimed embodiments require more features than are expressly recited in each claim.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather are to be accorded the widest scope consistent with the principles and novel features disclosed herein.

What is claimed is:

1. A system for detecting defects in an adhesion area comprising an adhesive mixed with a fluorescent material, comprising:

at least two modulated illumination devices for illuminating the fluorescent material in the adhesion area with a light of a predetermined wavelength;

a camera configured to capture an image of the illuminated adhesion area; and a processing device, communicatively coupled to the camera, the processing device being configured to process the captured image by applying one or more boundary areas to the captured image and determining an image characteristic within each of the boundary areas, wherein the image characteristic is used by the processing device to determine the presence of a defect in the adhesive.

2. The system of claim 1, wherein the processing device is configured to determine the presence of a defect in the adhesive, the defect comprising one of an excess of adhesive and an insufficient application of adhesive.

3. The system of claim 2, wherein the processing device is configured to determine the image characteristic comprising pixel coverage within each of the boundary areas.

4. The system of claim 3, wherein the processing device is configured to determine the presence of a defect in the adhesive utilizing one or more thresholds applied to the pixel coverage within each of the boundary areas.

5. The system of claim 2, wherein the processing device is configured to determine the image characteristic using machine vision.

6. The system of claim 5, wherein the processing device is configured to determine the image characteristic using machine vision comprising one of edge detection, grayscale matching and gradient matching.

7. The system of claim 1, wherein the camera comprises time-of-flight imaging.

8. A system for detecting defects in an adhesion area comprising an adhesive mixed with a fluorescent material, comprising:

one or more illumination devices for illuminating the fluorescent material in the adhesion area with a light of a predetermined wavelength;

a camera configured to capture an image of the illuminated adhesion area; and a processing device, communicatively coupled to the camera, the processing device being configured to process the captured image by applying one or more boundary areas to the captured image and determining an image characteristic within each of the boundary areas, wherein the image characteristic is used by the processing device to determine the presence of a defect in the adhesive, wherein the defect comprises one of an excess of adhesive and an insufficient application of adhesive, and wherein the processing device is configured to apply a mask to at least one other boundary area when determining an image characteristic within one of the boundary areas.

9. The system of claim 8, wherein the one or more illumination devices illuminate the fluorescing material using light modulated at one or more frequencies between 1-20 MHz.

10. The system of claim 8, wherein the processing device is configured to determine the image characteristic comprising pixel coverage within each of the boundary areas.

11. The system of claim 8, wherein the processing device is configured to determine the presence of a defect in the adhesive utilizing one or more thresholds applied to the pixel coverage within each of the boundary areas.

12. The system of claim 8, wherein the processing device is configured to determine the image characteristic using machine vision.

13. The system of claim 8, wherein the processing device is configured to determine the image characteristic using machine vision comprising one of edge detection, grayscale matching and gradient matching.

14. A method for detecting defects in an adhesion area comprising an adhesive mixed with a fluorescent material, comprising:

illuminating, by at least two modulated illumination devices, the fluorescent material in the adhesion area with a light of a predetermined wavelength;

capturing an image of the illuminated adhesion area by a camera;

processing, by a processing device communicatively coupled to the camera, the captured image by applying one or more boundary areas to the captured image;

determining, by the processing device, an image characteristic within each of the boundary areas; and using the image characteristic to determine the presence of a defect in the adhesive by the processing device.

15. The method of claim 14, wherein the defect comprises one of an excess of adhesive and an insufficient application of adhesive.

16. The method of claim 15, wherein determining the image characteristic comprises determining pixel coverage within each of the boundary areas.

17. The method of claim 16, wherein determining the presence of a defect in the adhesive comprises utilizing one or more thresholds applied to the pixel coverage within each of the boundary areas.

18. The method of claim 15, wherein determining the image characteristic comprises machine vision processing.

19. The method of claim 18, wherein the machine vision processing comprises one of edge detection, grayscale matching and gradient matching.

20. A method for detecting defects in an adhesion area comprising an adhesive mixed with a fluorescent material, comprising:

illuminating, by one or more illumination devices, the fluorescent material in the adhesion area with a light of a predetermined wavelength;

capturing an image of the illuminated adhesion area by a camera;

processing, by a processing device communicatively coupled to the camera, the captured image by applying one or more boundary areas to the captured image;

determining, by the processing device, an image characteristic within each of the boundary areas;

using the image characteristic to determine the presence of a defect comprising one of an excess of adhesive and an insufficient application of adhesive in the adhesive by the processing device; and applying a mask, by the processing device, to at least one other boundary area when determining an image characteristic within one of the boundary areas.

21. The method of claim 20, wherein capturing the image comprises time-of-flight imaging.

22. The method of claim 21, wherein illuminating the fluorescent material comprises light modulated at one or more frequencies between 1-20 MHz.

23. The method of claim 20, wherein determining the image characteristic comprises determining pixel coverage within each of the boundary areas.

24. The method of claim 23, wherein determining the presence of a defect in the adhesive comprises utilizing one or more thresholds applied to the pixel coverage within each of the boundary areas.

25. The method of claim 20, wherein determining the image characteristic comprises machine vision processing.

26. The method of claim 25, wherein the machine vision processing comprises one of edge detection, grayscale matching and gradient matching.

27. A system for detecting defects in an adhesion area comprising an adhesive mixed with a fluorescent material, comprising:
　one or more illumination devices for illuminating the fluorescent material in the adhesion area with a light of a predetermined wavelength;
　a modulator configured to modulate the light to a frequency between 1-20 MHz;
　a camera configured to capture an image of the illuminated adhesion area; and
　a processing device, communicatively coupled to the camera, the processing device being configured to process the captured image comprising the modulated light to determine an image characteristic, wherein the image characteristic is used by the processing device to determine the presence of a defect in the adhesive.

28. The system of claim 27, wherein the processing device is configured to apply at least one boundary area to the captured image, and further being configured to determine the presence of a defect from the boundary area, the defect comprising one of an excess of adhesive and an insufficient application of adhesive.

29. A system for detecting defects in an adhesion area comprising an adhesive mixed with a fluorescent material, comprising:
　one or more illumination devices for illuminating the fluorescent material in the adhesion area with a light of a predetermined wavelength;
　a camera configured to capture an image of the illuminated adhesion area; and
　a processing device, communicatively coupled to the camera, the processing device being configured to process the captured image by applying at least one mask to form at least two boundary areas, and determining an image characteristic within at least one of the at least two boundary areas, wherein the image characteristic is used by the processing device to determine the presence of a defect in the adhesive.

* * * * *